US00PP36849P2

(12) United States Plant Patent
Schoemaker

(10) Patent No.: US PP36,849 P2
(45) Date of Patent: Jul. 22, 2025

(54) ***HYDRANGEA* PLANT NAMED 'LC NO24'**

(50) Latin Name: *Hydrangea Paniculata*
Varietal Denomination: LC NO24

(71) Applicant: Alex Shoemaker Living Creations Holding B.V., Boskoop (NL)

(72) Inventor: Alex F. Schoemaker, Boskoop (NL)

(73) Assignee: Alex Schoemaker Living Creations Holding B.V. (NL)

( * ) Notice: Subject to any disclaimer, the term of this patent is extended or adjusted under 35 U.S.C. 154(b) by 0 days.

(21) Appl. No.: 18/985,518

(22) Filed: Dec. 18, 2024

(51) Int. Cl.
*A01H 5/00* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/00
See application file for complete search history.

*Primary Examiner* — Kent L Bell
(74) *Attorney, Agent, or Firm* — Cassandra Bright

(57) ABSTRACT

A new and distinct cultivar of *Hydrangea paniculata* plant named 'LC NO24' is disclosed, characterized by uniquely low growing, spreading and compact plants. Panicles are dense with flowers. Plants are very well branched, highly floriferous and flower from July to October. The sterile flowers have ornamental sepals that are apple green from the beginning to the end of the flower period. The new variety is a *Hydrangea*, typically produced as an outdoor ornamental plant.

4 Drawing Sheets

Latin name of the genus and species: *Hydrangea paniculata.*

Variety denomination: 'LC NO24'.

BACKGROUND OF THE INVENTION

The new cultivar is a product of a planned breeding program conducted by the inventor in Boskoop, the Netherlands. The inventor crossed the unpatented, proprietary seed parent '1525-2' with an unnamed, unpatented proprietary seedling as the pollen parent in 2018. The new cultivar 'LC NO24' was selected by the inventor in 2020 from seedlings developed from the 2018 crossing.

Asexual reproduction of the new cultivar 'LC NO24' was first performed during September of 2020 in in Boskoop, the Netherlands, by softwood cuttings. Through subsequent propagation, multiple additional generations have been reproduced, having shown that the unique features of this cultivar are stable and reproduced true to type.

The inventor has filed an application with the CPVO Aug. 11, 2024, having application number 2024/2619. The CPVO application references the first sale of the new variety which occurred in the Netherlands Feb. 23, 2024. The first sale was directly from the inventor. This disclosure falls within the exception allowed under 102(b)(1).

SUMMARY OF THE INVENTION

The cultivar 'LC NO24' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LC NO24'. These characteristics in combination distinguish 'LC NO24' as a new and distinct *Hydrangea* cultivar:

1. Low growing, compact plant which can be used as a groundcover.
2. Very well branched plants.
3. Highly floriferous plants.
4. Apple green sepals retaining color from the beginning to the end of the flowering period.
5. Flowering period from July to October.
6. Very full panicles, dense with flowers.

PARENT COMPARISON

Plants of 'LC NO24' are similar to plants of both parents in most horticultural characteristics, however, plants of 'LC NO24' differ in the following:

1. Plants of the new variety are smaller and more compact at maturity than plants of either parent.
2. Flower sepals of the new variety are a clearer green than sepals of either parent.
3. Green sepal color of the new variety is maintained longer than in either parent.

COMMERCIAL COMPARISONS

Plants of 'LC NO24' can be compared to plants of the commercial variety *Hydrangea* 'Jane', U.S. Plant Pat. No. 22,330. Plants of 'LC NO24' are similar to plants of 'Jane' in most horticultural characteristics, however, plants of 'LC NO24' differ in the following:

1. 'LC NO24' has flatter inflorescences than 'Jane'.
2. Plants of 'LC NO24' are more compact and spread wider than plants of 'Jane'.
3. The green sepals of 'LC NO24' stay green over the entire flowering period; the green sepals of this comparator fade before the end of the flowering period.

4. Inflorescences of 'LC NO24' are denser than inflorescences of 'Jane'.

Plants of the new cultivar *Hydrangea* 'LC NO24' can be compared to the commercial variety *Hydrangea paniculata* 'Mojito', unpatented. Plants of 'LC NO24' are similar to plants of 'Mojito' in most horticultural characteristics, however, plants of 'LC NO24' differ in the following:

1. 'LC NO24' has flatter inflorescences than 'Mojito'.
2. Plants of 'LC NO24' are more compact and spread wider than plants of 'Mojito'.
3. The green sepals of 'LC NO24' stay green over the entire flowering period; the green sepals of this comparator fade before the end of the flowering period.
4. Inflorescences of 'LC NO24' are denser than inflorescences of 'Mojito'.

BRIEF DESCRIPTION OF THE PHOTOGRAPHS

The accompanying photograph in FIG. 1 illustrates in full color a typical plant of 'LC NO24' grown in Boskop, the Netherlands. This plant is approximately 2 years old, grown in a 28 cm pot.

Figure 1:
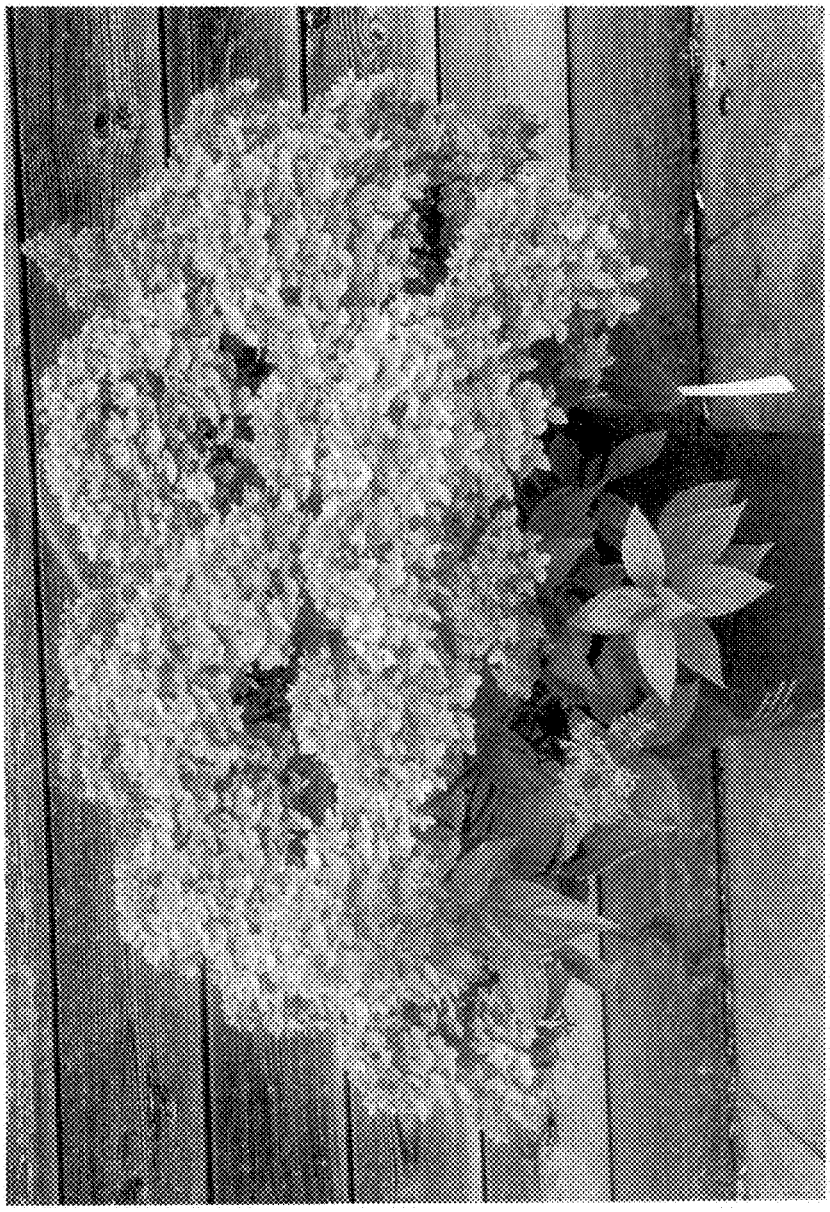
Figure 2:
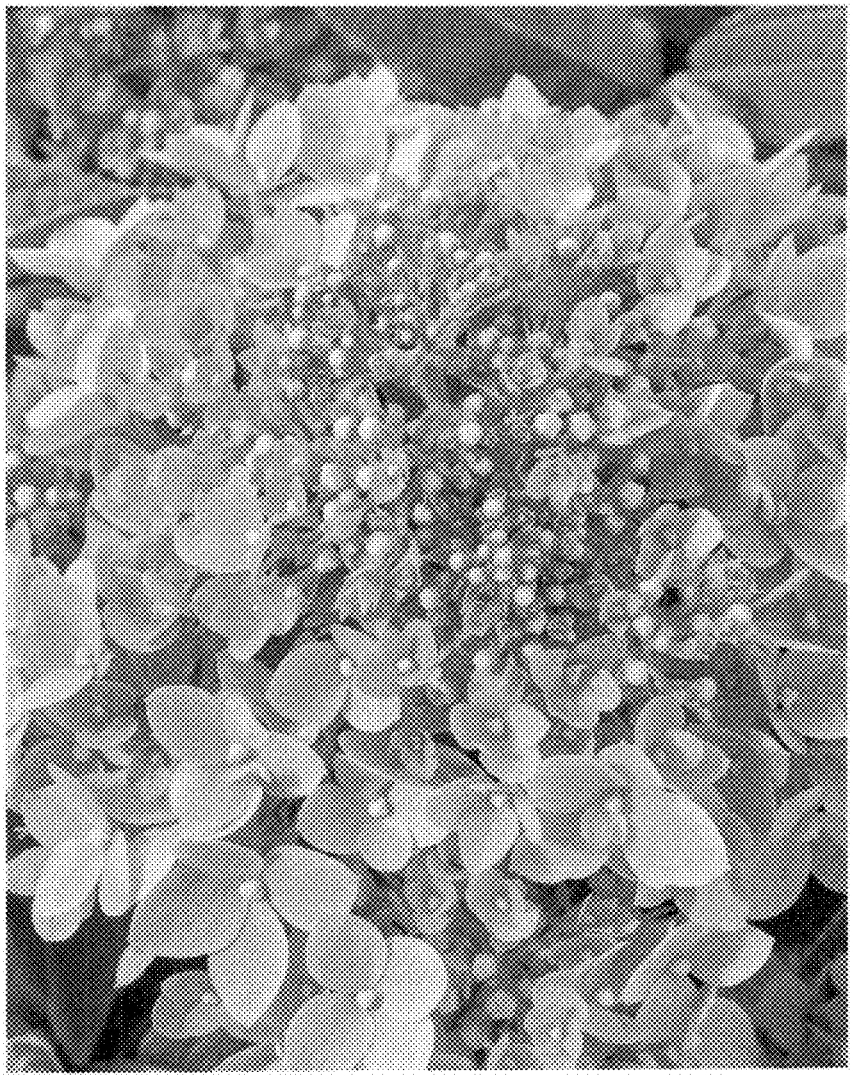
FIG. 2 illustrates in full color a close-up view of a typical slightly immature inflorescence of 'LC NO24', during July.
Figure 3:
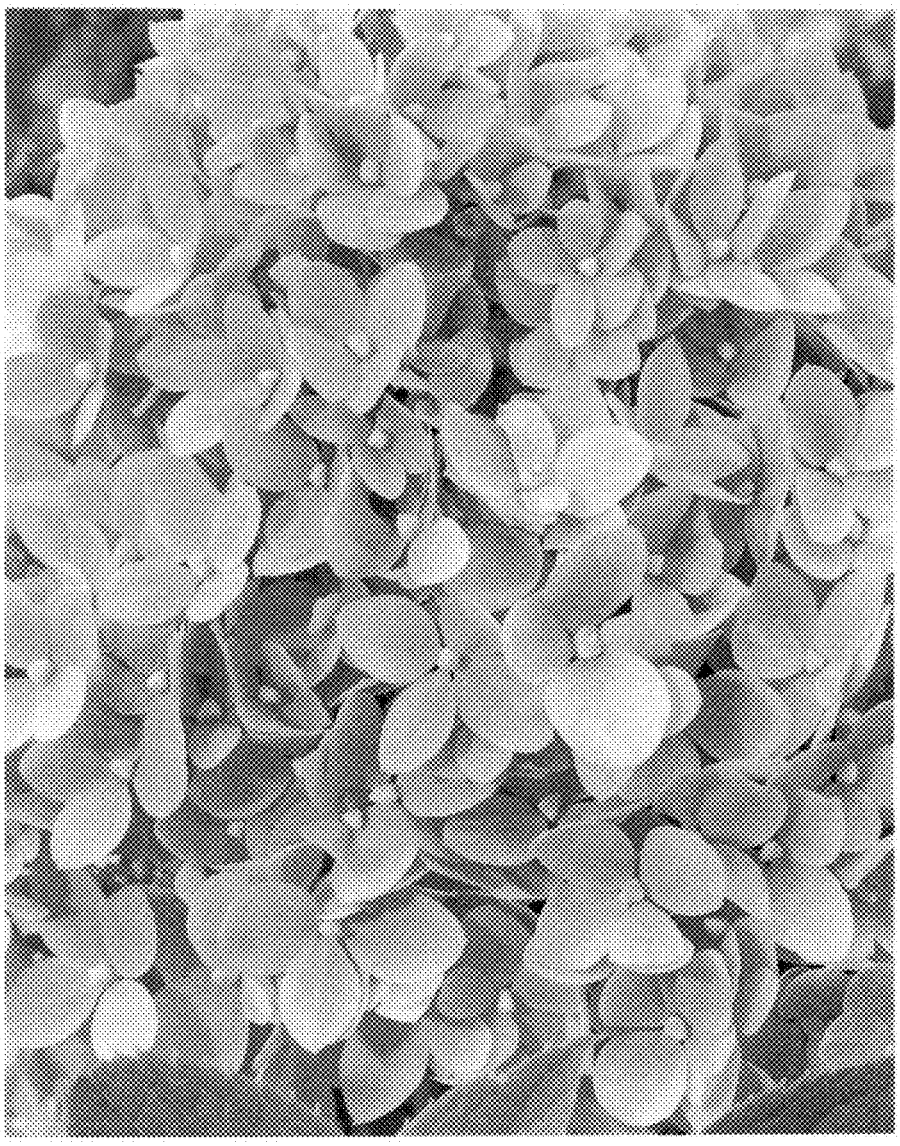
FIG. 3 illustrates the same inflorescence of 'LC NO24', during August.
Figure 4:
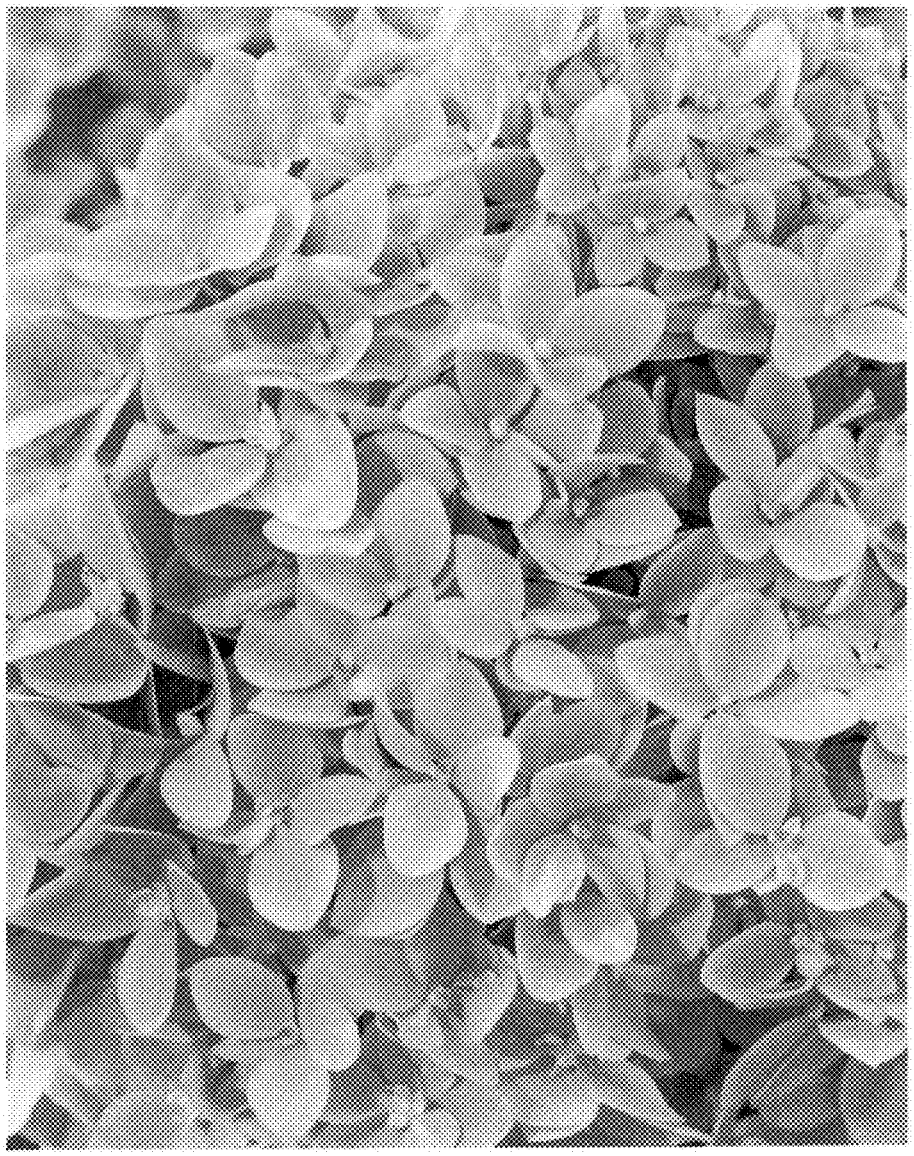
FIG. 4 is the same inflorescence photographed in September.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'LC NO24' plants grown outdoors in Boskoop, the Netherlands in a 28 cm pot. The plants were about 2-years old. Temperatures ranged from about 5° C. to 10° C. at night to 18° C. to 27° C. during the day. No artificial light, photoperiodic treatments were given to the plants. Measurements and numerical values represent averages of typical plant types.

Botanical classification: *Hydrangea paniculata* 'LC NO24'.

PROPAGATION

Typical method: Softwood cuttings.

Roots: Thin, freely branching, fibrous, moderately dense. Creamy white to off brown in color, not accurately measured with R.H.S. chart.

PLANT

Growth habit: Compact and spreading. Deciduous flowering shrub.

Shape: Flattened globular.

Height: 39 cm.

Plant spread: 71 cm.

Plant vigor: Moderate.

Branches:

*Branching*.—Basal, very free branching.

*Number of branches*.—3 main stems, each with 12 lateral branches.

*Shape*.—Rounded.

*Color*.—Immature: RHS Yellow-Green 144A and 144B. Mature: RHS Grey-Brown N199A and N199B.

*Length*.—27 cm.

*Width*.—7 to 10 mm.

*Strength*.—Strong.

*Texture*.—Lightly pubescent and covered in lenticels (moderately). Lenticels about 1 cm in diameter, colored near Greyed-Orange 164B.

*Internode length*.—4 cm.

FOLIAGE

Leaf:

*Arrangement*.—Opposite.

*Shape*.—Ovate.

*Length*.—9 cm.

*Width*.—5 cm.

*Apex*.—Acuminate.

*Base*.—Rounded.

*Margin*.—Serrate. Dense, small serrations.

*Texture of top surface*.—Slightly pubescent.

*Texture of bottom surface*.—Slightly pubescent.

*Color*.—Young Foliage, Upper Side: RHS Green 138A. Young Foliage, Under Side: RHS Green 138B. Mature Foliage, Upper Side: RHS Green NN137A. Mature Foliage, Under Side: RHS Yellow-Green 146B.

Venation:

*Type*.—Pinnate.

*Color*.—Mature, Upper Side: RHS Yellow-Green 144B. Mature, Under Side: RHS Yellow-Green 145A and 145B.

Petiole:

*Length*.—1.9 cm.

*Width*.—3 mm.

*Color: Upper Side: RHS Yellow Green* 144B with Greyed-Orange 176A. Under Side: RHS Yellow-Green 145A.

*Texture*.—Upper Side: Lightly pubescent. Under Side: Lightly pubescent.

INFLORESCENCE

Natural flowering season: July to October.

Inflorescence type: Mophead.

Lastingness: About 12 weeks.

Conspicuousness of fertile flowers: Moderately conspicuous.

Panicle:

*Shape*.—Broad conical.

*Height*.—16 cm.

*Diameter*.—18 cm.

Fragrance: Light, sweet.

Sterile flowers:

*Flowers per inflorescence*.—400 to 500.

*Aspect*.—Upward and outward.

*Shape*.—Rotate.

*Length*.—7 mm.

*Diameter*.—2 cm.

*Persistence*.—Persistent.

Bud:
*Length.*—2 mm.
*Diameter.*—2 mm.
*Shape.*—Ovoid.
*Color.*—RHS Yellow-Green 145D, with a hint of Red-Purple 68A.

Petals:
*Number.*—4.
*Arrangement.*—Rotate.
*Shape.*—Ovate.
*Tip.*—Acute.
*Base.*—Cuneate.
*Margin.*—Entire.
*Length.*—4 mm.
*Width.*—1.5 mm.
*Texture.*—Upper side: Glabrous. Under side: Glabrous.
*Color.*—Upper Side: RHS White NN155D occasionally blotched Red-Purple 68A. Under Side: RHS White NN155D occasionally blotched Red-Purple 68A.

Sepals:
*Number.*—4 or 5.
*Arrangement.*—Rotate.
*Shape.*—Ovate.
*Tip.*—Acute.
*Base.*—Tapered.
*Margin.*—Entire.
*Length.*—10 mm.
*Width.*—6 to 7 mm.
*Texture.*—Upper side: Glabrous. Under side: Glabrous.
*Color.*—When Opening, Upper Side: RHS Green 143B. When Opening, Under Side: RHS Green 143C. Fully Opened, Upper Side: RHS Green 143B and 143C flushed 144C. Fully Opened, Under Side: RHS Yellow-Green 145A flushed 144B.

Pedicel:
*Length.*—2 cm.
*Diameter.*—1 mm.
*Strength.*—Moderately strong.
*Texture.*—Very slightly pubescent.
*Color.*—RHS Yellow-Green 145A.

Fertile flowers:
*Flowers per inflorescence.*—About 150.
*Aspect.*—Upright.
*Arrangement.*—Rotate.
*Length.*—5 mm.
*Diameter.*—5 mm.

Bud:
*Length.*—1.5 mm.
*Diameter.*—1.5 mm.
*Bud shape.*—Globose.
*Bud color.*—RHS Yellow-Green 145A.

Petals:
*Number per flower.*—5.
*Arrangement.*—Rotate.
*Shape.*—Ovate.
*Tip.*—Acute.
*Base.*—Cuneate.
*Margin.*—Entire.
*Length.*—4 mm.
*Width.*—1.5 mm.
*Texture.*—Upper Side: Glabrous. Under Side: Glabrous.
*Color.*—Upper Side: RHS White N155D with Yellow-Green 145D. Under Side: RHS Yellow-Green 145D.

Fertile flower sepals:
*Number per flower.*—5.
*Arrangement.*—Rotate.
*Shape.*—Deltoid.
*Tip.*—Acuminate.
*Base.*—Broad cuneate.
*Margin.*—Entire.
*Length.*—1.5 mm.
*Width.*—1 mm.
*Texture.*—Upper Side: Glabrous. Under Side: Glabrous.
*Color.*—Upper Side: RHS Yellow-Green 145A. Under Side: RHS Yellow-Green 145A.

Fertile flower pedicel:
*Length.*—1.5 mm.
*Diameter.*—1 mm.
*Strength.*—Moderate.
*Texture.*—Slightly pubescent.
*Color.*—RHS Yellow-Green 145A.

REPRODUCTIVE ORGANS

Sterile flower: Androecium only.

Stamens:
*Number.*—Most commonly 8.
*Filament length.*—2 mm.
*Filament color.*—RHS White NN155D.

Anthers:
*Shape.*—Globose.
*Length.*—0.5 mm.
*Color.*—RHS Greyed-Orange 163C.
*Pollen.*—Moderate quantity. Colored near Greyed-Orange 163C.

Fertile flower:

Stamens:
*Number.*—Average 10.
*Filament length.*—6 mm.
*Filament color.*—RHS White NN155C.

Anthers:
*Shape.*—Broad oblong.
*Length.*—0.5 mm.
*Color.*—RHS Greyed-Orange 163C.
*Pollen amount.*—Scant. Colored near Greyed-Orange 163C.

Pistil:
*Number.*—3.
*Length.*—1.5 mm.

Stigma:
*Shape.*—Club-shaped.
*Color.*—RHS Yellow-Green 145C.
*Style length.*—1 mm.
*Style color.*—RHS White NN155D.
*Ovary color.*—Yellow-Green 145D.

SEEDS

Not observed.

OTHER CHARACTERISTICS

Disease resistance: Neither resistance nor susceptibility to the normal diseases and pests of *Hydrangea* has been observed.

Cold tolerance: Hardy to −25° C.

What is claimed is:

1. A new and distinct cultivar of *Hydrangea* plant named 'LC NO24' as herein illustrated and described.

* * * * *